(12) United States Patent
Osuna Carrillo de Albornoz et al.

(10) Patent No.: US 8,821,886 B2
(45) Date of Patent: Sep. 2, 2014

(54) RECOMBINANT ANTIGEN

(75) Inventors: Antonio Osuna Carrillo de Albornoz, Granada (ES); Miguel Burgos Poyatos, Granada (ES); Jennifer Solano Parada, Granada (ES); Fatima Brazil Dos Santos, Granada (ES)

(73) Assignee: Universidad de Granada, Granada (ES)

( * ) Notice: Subject to any disclaimer, the term of this patent is extended or adjusted under 35 U.S.C. 154(b) by 528 days.

(21) Appl. No.: 12/920,027

(22) PCT Filed: Feb. 19, 2009

(86) PCT No.: PCT/ES2009/070035
§ 371 (c)(1),
(2), (4) Date: Dec. 8, 2010

(87) PCT Pub. No.: WO2009/106665
PCT Pub. Date: Sep. 3, 2009

(65) Prior Publication Data
US 2011/0123519 A1 May 26, 2011

(30) Foreign Application Priority Data
Feb. 27, 2008 (ES) .................................. 200800565

(51) Int. Cl.
*A61K 39/00* (2006.01)
*A61K 39/002* (2006.01)

(52) U.S. Cl.
USPC ..................................... 424/185.1; 424/191.1

(58) Field of Classification Search
None
See application file for complete search history.

(56) References Cited

U.S. PATENT DOCUMENTS

| 5,679,354 | A | | 10/1997 | Morein et al. |
| 5,955,089 | A | * | 9/1999 | Briles et al. ................. 424/244.1 |
| 6,027,732 | A | | 2/2000 | Morein et al. |
| 6,464,979 | B1 | | 10/2002 | Murdin et al. |
| 6,607,732 | B2 | | 8/2003 | Morein et al. |
| 6,747,137 | B1 | * | 6/2004 | Weinstock et al. ........... 536/23.1 |

FOREIGN PATENT DOCUMENTS

| ES | 2 029 758 | 9/1992 |
| ES | 2 195 169 | 12/2003 |
| ES | 2 199 346 | 2/2004 |
| ES | 2 210 495 | 7/2004 |
| ES | 2 214 608 | 9/2004 |
| ES | 2 284 265 | 11/2007 |
| WO | WO 93/23542 | 11/1993 |
| WO | WO 97/30727 | 8/1997 |
| WO | WO 00/07621 | 2/2000 |

OTHER PUBLICATIONS

Plotkin et al (Vaccines, W. B. Saunders Company, 1988, p. 571).*

Bethony et al., "Vaccines Against Blood-Feeding Nematodes of Humans and Livestock." *Parasitology* vol. 133, 2006, p. S63-S79.

Bungiro, Jr. et al., "Purification and Molecular Cloning of and Immunization with *Ancyclostoma ceylanicum* Excretory-Secretory Protein 2, an Immunoreactive Protein Produced by Adult Hookworms." *Infection and Immunity* vol. 72, No.4, Apr. 2004, p. 2203-2213.

Demana et al., "Pseudo-Ternary Phase Diagrams of Aqueous Mixtures of Quil A, Cholesterol and Phospholipid Prepared by the Lipid-Film Hydration Method." *International Journal of Pharmaceutics*, vol. 207, 2004, p. 229-239.

Endoh et al., "Antibody Coating of Liposomes with 1-Ethyl-3-(3-Dimethyl-Aminopropyl) Carbodiimide and the Effect on Target Specificity." *Journal of Immunological Methods*, vol. 44, 1981, p. 79-85.

Faux et al., "More on Target with Protein Phosphorylation: Conferring Specificity by Location." *TIBS*, vol. 21, Aug. 1996, p. 312-315.

Fujiwara et al., "Protection Against Hookworm Infection Elicited by Vaccination with Recombinant Ac-16 is Mediated by Reduction of Worm Fecundity and Canine Host Blood Loss." *Clin. Vaccine Immunol.* vol. 14(3), Mar. 2007, p. 281-287.

Iosef et al., "Systemic and Intestinal Antibody Secreting Cell Responses and Protection in Gnotobiotic Pigs Immunized Orally with Attenuated Wa Human Rotavirus and Wa 2/6-Rotavirus-Like-Particles Associated with Immunostimulating Complexes." *Vaccine*, vol. 20, 2002, p. 1741-1753.

Islam et al., "Pyrophosphatase of the Roundworm *Ascaris suum* Plays an Essential Role in the Worm's Molting and Development." *Infection and Immunity*, vol.73, No. 4, Apr. 2005, p. 1995-2004.

Kerepesi et al., "DNA Immunization with $Na^+$-$K^+$ ATPase (*Sseat-6*) Induces Protective Immunity to Larval *Strongyloids stercoralis* in Mice." *Infection and Immunity*, vol. 73. No. 4. Apr. 2005, p. 2298-2305.

Miller et al., "Immunological Aspects of Nematode Parasite Control in Sheep." *Journal of Animal Science*, vol. 84 (*E.Suppl.*), 2006, p. E124-E132.

Ramachandran et al., "The Larval Specific Lymphatic Filarial ALT-2: Induction of Protection Using Protein or DNA Vaccination." *Microbiol. Immunol.*, vol. 48(12), 2004, p. 945-955.

Redmond et al., "Protection Studies in Sheep Using Affinity-Purified and Recombinant Cysteine Proteinases of Adult *Haemonchus contortus.*" *Vaccine*, vol. 22, 2004, p. 4253-4261.

Reszka et al., "*Haemonchus contortus*: Characterization of the Baculovirus Expressed Form of Aminopeptidase H11." *Experimental Parasitology*, vol. 117, 2007, p. 208-213.

Robinson et al., "High Levels of Protection Induced by a 40-mer Synthetic Peptide Vaccine Against the Intestinal Nematode Parasite *Trichinella spiralis.*" *Immunology* vol. 86, 1995, p. 495-498.

Tsuji et al., "Recombinant *Ascaris* 16-Kilodalton Protein-Induced Protection against *Ascaris suum* Larval Migration after Intranasal Vaccination in Pigs." *JID* vol. 190, Nov. 15, 2004, p. 1812-1820.

(Continued)

Primary Examiner — Albert Navarro
(74) Attorney, Agent, or Firm — Merchant & Gould P.C.

(57) ABSTRACT

Recombinant protein of the catalytic subunit of the phosphatase Serine/threonine protein of *Angiostrongylus costaricensis*, and active peptides used in the production of an intranasal anthelmintic vaccine.

4 Claims, 1 Drawing Sheet

(56) References Cited

OTHER PUBLICATIONS

Vercauteren et al., "Vaccination with an *Ostertagia ostertagi* Polyprotein Allergen Protects Calves against Homologous Challenge Infection." *Infection and Immunity*, vol. 72, No. 5, May 2004, p. 2995-3001.

Yanming, et al., "Vaccination of Goats with Recombinant Galectin Antigen Induces Partial Protection Against *Haemonchus contortus* Infection." *Parasite Immunology*, vol. 29, 2007, p. 319-326.

Zhan et al. "Biochemical Characterization and Vaccine Potential of a Heme-Binding Glutathione Transferase from the Adult Hookworm *Ancylostoma caninum.*" *Infection and Immunity*, vol. 73, No. 10, Oct. 2005, p. 6903-6911.

International Search Report for Application No. PCT/ES2009/070036 dated May 20, 2009.

J. Solano-Parada, et al., "Effectiveness of intranasal vaccination against *Angiostrongylus constaricensis* using a serine/threonine phosphatase 2 A synthetic peptide and recombinant antigens", *Vaccine* 28 (2010), pp. 5185-5196.

Pinto et al., "Effect of *Angiostrongylus constaricensis* extract on eosinophilic pulmonary response in BALB/c mice", *Parasitology Research* (2006), vol. 98, No. 4, pp. 295-298.

Supplementary European Search Report dated Mar. 19, 2012 from EP 09 71 4303.

\* cited by examiner

| | | |
|---|---|---|
| A costaricensis<br>PP2Ac<br>Consensus | V V D E F c t a h N i D L I I R A H q I T A E m V<br>V V D E F l e r n N i D L i i R A H e       v V<br>* * * *     * * *   * * *     * | 25<br>224 |
| A costaricensis<br>PP2Ac<br>Consensus | y g G Y r i F A g G r L v T i F S A P N Y q n m m<br>d d G Y e f F A d G k L i T v F S A P N Y c g q f | 50<br>249 |
| A costaricensis<br>PP2Ac<br>Consensus | . N d g c V m r i k r d L t a n F i i f<br>G N a a a V l k v d g n L k i t F v q l | 69<br>269 |
| A costaricensis<br>Smart00156<br>Consensus | V V D E F c t n h N i d L I I R A H Q I T A E m V<br>V V D E F l k k n N i k L i R A H Q       v V | 25<br>222 |
| A costaricensis<br>Smart00156<br>Consensus | y g G Y r i F A g G r L V T I F S A P N Y q n m m<br>d d G Y e f F A d G k L V T I F S A P N Y c g r f | 50<br>247 |
| A costaricensis<br>Smart00156<br>Consensus | . N d g c V m r i k r d L t a n F i i F r P x<br>G N k a a V l k v d k n L k l s F e q F k P g | 72<br>270 |

FIGURE 1

```
AF496634.1    WQANTRGYSYVPYQDVVFETCQFLHIDLIARAHQV----VQDGYEFFAHKRMVTIFSAPH 269
AM261207.1    WQPIHRSLSYTFGVDVVNDMCQKLDIDLIARAHQV----VQDGYEFFAHPFLVTIFSAPH 270
AM691045.1    FQALMRSASYGFGPDVLAKYCQTINIDLVARAHQV----VQDGYEFFGGPFLVTIFSAPH 266
EF066638.1    WGELDRFVSFTFGPDVVAKFLTRHDLDLICRAHQV----VEDGYEFFAKPQLVTLFSAPH 142
AM041130.2    ---------------VVDEFCTNRNIDLILRAHQITAEMVGGYRIFAGGRLVTTFSAPN  45
NM_074208.2   WSLSAFSTSFSFDDLTIERFCQDNGLDLIVRAHQISSEMIPGGHKWRANGRMVTTFSAAN 300
                                 :  .   *  :  *  *:  :          : . :  ::**:*:.

AF496634.1    YCGQFDNFAATMKVSEDLVHHPAMYKPTAPALPMAAGVSRAS----------------- 311
AM261207.1    YCGQFDNAAAMMNVDEGLVCTPQILRPSVPEHFPTG--TK------------------- 308
AM691045.1    YCGQFDNAAAMMTVDENIQGHPETFRDSVCKPQPFTIPTCVGSPAAPDCQ--------- 316
EF066638.1    SPQEFDNAGAMMSVLETLMCHFQVLPGEKKGETQYGNFTAGRPVTPPRNSDFGKFAPE 201
AM041130.2    YQN-MMNDGCVMRTKRDLTANFIIFRPVVR--PH-------------------------  76
NM_074208.2   YLS-MGNDSCVIRTDEQKIMQFCLLRPVKKSPKH------------------------- 333
                 :*  ..  ::   *   :  :*  :
```

FIGURE 2

RECOMBINANT ANTIGEN

This application is a National Stage Application of PCT/ES2009/070036, filed 19 Feb. 2009, which claims benefit of Serial No. P200800565, filed 27 Feb. 2008 in Spain and which applications are incorporated herein by reference. To the extent appropriate, a claim of priority is made to each of the above disclosed applications.

The present invention refers to nucleic acids which codify the catalytic subunit of the protein Serine/threonine phosphatase of *Angiostrongylus costarricensis*, the protein, synthetic peptides and antibodies generated against this protein and these peptides. The present invention also refers to a composition used as immunogen, generating an immune response against the infection of nematode parasites.

PRIOR STATE OF THE ART

Filum Nematoda encompasses many parasites important in both medicine and veterinary such as: *Ascacris lumbricoides, Trichuris trichura, Enterobius vermicularis, Necator americanus, Ancylostoma duodenale* and *Strongyloides stercoralis*, which constitute a genuine public health problem widely spread in the world. Many species cause great economic losses in stockbreeding, such as for example: *Teladorsagia circumcincta, T. trifurcata, Trichostrongylus vitrinus, T. capricola, Nematodirus filicollis, Strongyloides ramsoni, Oesophagostomum* spp, *Ascaris suum*, among others.

Most nemathelminthes parasites have in common their passing through the intestinal wall towards different organs or their fixation at the level of the intestinal mucosa, originating weight loss, diarrhea, and in some cases hemorrhage. Although mortality is relatively low, morbidity is very high.

Anthelmintic drugs currently used are chemical compounds with low efficacy, due to the growing appearance of resistant nematodes. This resistance to anthelmintic drugs produces the need to develop more effective and specific antiparasitic drugs. Vaccines have been considered the best alternative to antiparasitic drugs for the control of gastrointestinal nematodes. In any case, although there exist several antigens providing different degrees of protection, there are no vaccines against nematode parasites.

Current studies aim at the search for proteins with immunoprotective characteristics as possible candidates to be used in vaccines.

Numerous works have been published where there are described total fractions, excreted antigens, purified and/or recombinant antigens, as well as different adjuvants or forms of evaluation of the protection (Bethony et al., Vaccines against blood-feeding nematodes of humans and livestock. *Parasitology*. 2006: 133 S63-79; Miller & Horoho, Immunological aspects of nematode parasite control in sheep. *J Anim Sci*. 2006. April: 84 Suppl: E124-32).

One of the first studies on immunoprotection with synthetic peptides was performed by Robinson et al., (High levels of protection induced by a 40-mer synthetic peptide vaccine against the intestinal nematode parasite *Trichinella spiralis*. *Immunology*. 1995. December; 86(4):495-8), where the use of a 40-aminoacid peptide (100 µg) subcutaneously combined with Freund's coadjuvant is described.

The coadjuvant used, the inoculation path and the protein concentration are important factors to consider in vaccine development. Among the most widely used coadjuvants in these assays we can find Freund's coadjuvant, QuilA, aluminum hydroxide, beryllium hydroxide, etc. Some of them have shown to be ineffective or their used is currently not recommended.

Protection levels found so far are generally low, for example in studies performed with *Haemonchus contortus*: Yanming et al., (Vaccination of goats with recombinant galectin antigen induces partial protection against *Haemonchus contortus* infection. *Parasite Immunol*. 2007. June; 29(6): 319-26) rHco-gal-m and rHco-gal-f proteins have been used with Freund's coadyuvant in goats, obtaining a 37% reduction of the elimination of eggs in feces, while Reszka et al. 2007 used a recombinant aminopeptidase H11 (300 µg) intramuscularly in sheep, obtaining a 30% reduction of the parasite load. In previous studies Redmond and Knox (Protection studies in sheep using affinity-purified and recombinant cysteine proteinases of adult *Haemonchus contortus*. 2004. Vaccine 22:4252-4261) obtained a 38% reduction of the parasite load in sheep using a cysteine proteinase. Although for other nematodes it was obtained a 75% protection in rats against *Brugia malayi* using the recombinant Bm-ALT-2 protein (Thirugnanam et al., *Brugia malayi*: comparison of protective immune responses induced by Bm-alt-2 DNA, recombinant Bm-ALT-2 protein and prime-boost vaccine regimens in a jird model. *Exp Parasitol*. 2007. August; 116(4):483-91. Epub 2007 Mar. 6) and a 70% protection using an inorganic Pyrophosphatase against *Ascaris suum* in BALB/c (Islam, Pyrophosphatase of the roundworm *Ascaris suum* plays an essential role in the worm's molting and development. *Infect. Immun*. 2005. April; 73(4):1995-2004). Several proteins have been tested against *Ancylostoma caninum* as candidates for vaccines, Fujiwara et. al., (Protection against hookworm infection elicited by vaccination with recombinant Ac-16 is mediated by reduction of Word fecundity and canine host blood loss. *Clin Vaccine Immunol*. 2007. March; 14(3):281-287) obtained a 63% reduction of eggs found in feces of dogs immunized with Ac-16 protein, Zhan et al., (Biochemical characterization and vaccine potential of a heme-binding glutathione transferase from the adult hookworm *Ancylostoma caninum*. *Infect Immun*. 2005 October; 73(10):6903-11) used a glutathion S-transferase in dogs obtaining a 34% reduction and immunizing with a recombinant metalloproteinase, Hotez et al. (Effect of vaccination with a recombinant fusion protein encoding an astacinlike metalloprotease (MTP-1) secreted by host-stimulated *Ancylostoma caninum* third-stage infective larvae. *J. Parasitol*. 2003 August; 89(4):853-5) obtained a 32.3% reduction of eggs in feces.

The greatest knowledge regarding the parasite-host relation has enabled the identification of antigens considered vital for the survival of nematode such as excretory-secretory proteins, Vercauteren et al. (Vaccination with an *Ostertagia ostertagi* polyprotein allergen protects calves against homologous challenge infection. *Infect Immun*. 2004 May; 72(5):2995-3001) used *Ostertagia* polyprotein allergen (OPA) in its native and recombinant form against *Ostertagia ostertagi*, obtaining a 60% reduction of eggs in feces in beef cattle in the group inoculated with the native protein. Bungiro et al. (Purification and molecular cloning of and immunization with *Ancylostoma ceylanicum* excretory-secretory protein 2, an immunoreactive protein produced by adult hookworms. *Infect Immun*. 2004 April; 72(4):2203-13) also used an excretory-secretory protein, AceES-2 against *Ancylostoma ceylanicum* in hamster, obtaining a reduction of anemia when orally providing said native protein.

Tsuji et al. (Recombinant *Ascaris* 16-Kilodalton protein-induced protection against *Ascaris suum* larval migration after intranasal vaccination in pigs. *J Infect Dis*. 2004 Nov. 15; 190(10):1812-20. Epub 2004 Sep. 30) reached a 58% protection inoculating pigs during intranasal vaccination with the recombinant As16 protein combined with the cholera toxin.

Besides the proteins, there have also been used genes as immunomodulators, Wang et al. (Vaccination of mice with DNA vaccine induces the immune response and partial protection against *T. spiralis* infection. *Vaccine*. 2006 Feb. 20; 24(8):1205-12. Epub 2005 Sep. 19) obtained a significant reduction of *Trichinella spiralis* larvae in muscle after inoculation of rats with the TspE1 gene, this type of study has also been performed against *Onchocerca vulvolus* using the ALT-2 gene (Ramachandran et al. The larval specific lymphatic filarial ALT-2: induction of protection using protein or DNA vaccination. *Microbiol. Immunol.* 2004; 48(12):945-55) and against *Strongyloides stercoralis* using the Sseat-6 gene corresponding to an ATPase, with which high protection was obtained (Kerepesi et al., DNA immunization with Na+—K+ ATPase (Sseat-6) induces protective immunity to larval *Strongyloides stercoralis* in mice. *Infect Immun.* 2005 April; 73(4):2298-305).

The most effective vaccine up to this date is membrane 110 KDa protein with aminopeptidase activity A and M was called H11 (Graham et al., Recombinant DNA molecules encoding aminopeptidase enzymes and their use in the preparation of vaccines against helminth infections. Patent Application No. WO93/23542.)

Although there are many assays of vaccine models, there are only two commercial vaccines against lung nematode parasites Bovilis® Huskvac (Intervet) and Dictol (Schering Plough Animal Health). Even though there exist some more against protozoos important in the veterinary field such as: against coccidiosis in birds Paracox (Schering Plough Animal Health), Coccivax (Schering Plough Animal Health), Livacox (Biopharm, Czech Republic) and Immucox (Vetech); against toxoplasmosis in sheep Toxovax (Intervet); against Giardiasis in dogs Giardia (Vax Fort Dodge), against anaplasmosis in beef cattle (Anaplaz Fort Dodge).

However, given the low efficacy of the vaccines produced using other proteins as immunogenic component, and the need to find effective vaccines against lung nematodes, it is necessary to find other proteins and formulations which are effective against said parasites.

EXPLANATION OF THE INVENTION

The authors of the present invention have found a protein which enables the production of an immunogenic composition to produce a vaccine with an immunoprotective activity which attains protection with an 80-100% activity, depending on the form and type of immunization.

Thus, using the catalytic subunit of the protein phosphatase serine/threonine of *Angiostrongylus costaricensis*, producing the protein in a recombinant, and synthetic, manner, a peptide capable of acting as immunogen, it is possible to attain protection levels much higher than those obtained so far.

According to an aspect of the present invention, it is provided a peptide which is selected from a list consisting of:
 a) peptide essentially consisting of the amino acid sequence of SEQ ID No.: 1
 b) fragment of the amino acid sequence SEQ ID No.: 1 essentially consisting of SEQ ID No.: 2, SEQ ID No.: 3, SEQ ID No.: 4 or SEQ ID No.: 5
 c) peptide whose amino acid sequence has an identity of at least 80% with the SEQ ID No.: 1, SEQ ID No.: 2, SEQ ID No.: 3, SEQ ID No.: 4 or SEQ ID No.: 5
for its use as medicine.

The term "peptide essentially consisting of", as defined in this memory, refers to the fact that the peptide comprises a part, or the total, of a particular amino acid sequence, and whose main function is the generation of immunity. Thus, it can be a fusion polypeptide, which extends the immunogenicity of the entire or a part of the catalytic subunit of the protein Serine/threonine phosphatase of *Angiostrongylus costarricensis*, and an additional polypeptide.

The term "identity", as used in this memory, refers to the proportion of identical amino acids between two amino acid sequences being compared.

When we compare the sequence of the catalytic subunit of the protein Serine/threonine phosphatase of *Angiostrongylus costarricensis* with the sequence of the same protein in other species of nematodes (FIG. 2), it is evident that there exist certain regions in which they are more conserved than others. This information can indicate that these areas are crucial to maintain the structure or function of the protein. Both the active regions determining the specificity of the serine-proteases and the cysteines conserved between which there are established disulfide bridges, important for the conformation of the protein will be perfectly conserved between both proteins, while in other regions the divergence is more apparent.

The term "homology", as used in this memory, refers to the similarity between two structures due to a common evolutionary origin, and more specifically, to the similarity between two amino acids of two or more proteins or amino acid sequences.

As two proteins are considered homologous if they have the same evolutionary origin or if they have similar function and structure, in general, it is assumed that similarity or identity values higher than 30% indicate homologous structures. We can consider, therefore, that identity percentages of, at least, 80%, will include the active regions conserved between nematodes and capable of generating immunity.

Preferably, in a preferred embodiment of this aspect of the invention, the amino acid sequence of the peptide will present an identity of at least, 90% with SEQ ID NO: 1, SEQ ID NO:2, SEQ ID NO: 3, SEQ ID NO:4 or SEQ ID NO:5. More preferably, in another preferred embodiment of this aspect of the invention, the amino acid sequence of the peptide will present an identity of at least, 95% with SEQ ID NO: 1, SEQ ID NO:2, SEQ ID NO: 3, SEQ ID NO:4 or SEQ ID NO:5. Even more preferably, in an preferred embodiment of this aspect of the invention, the amino acid sequence of the peptide will present an identity of at least, 98% with SEQ ID NO: 1, SEQ ID NO:2, SEQ ID NO: 3, SEQ ID NO:4 or SEQ ID NO:5.

In the context of the present invention, the catalytic subunit of the protein phosphatase serine/threonine of *Angiostrongylus costaricensis* is defined by a sequence of nucleotides or polynucleotides, constituting the codifying sequence of the protein, and which would comprise several variants coming from:
 a) molecules of nucleic acid which codify a polypeptide comprising the amino acid sequence of SEQ ID NO: 1 (Access Number in GenBank AM041130),
 b) molecules of nucleic acid whose complementary chain forms a hybrid with the polynucleotide sequence of a),
 c) molecules of nucleic acid whose sequence differs from a) and/or b) due to the degeneration of the genetic code,
 d) molecules of nucleic acid which codify a polypeptide comprising the amino acid sequence with an identity of at least 80%, 90% or 95%, with the SEQ ID NO: 1 in which the polypeptide codified by said nucleic acids has the immunogenic activity of the catalytic subunit of the phosphatase serine/threonine protein of *Angiostrongylus costaricensis*.

The design of synthetic peptides is known in the state of the art. Thus, the analysis of the data of the experimentally determined antigenic sites has revealed that the Cys, Leu and Val hydrophobic residues, if they occur in the surface of the protein, have a great tendency to form part of the antigenic determinants. In this way, semi-empiric methods have been determined which use the physico-chemical properties of the amino acid residues and their frequencies and occurrence in epitope segments experimentally known to determine the antigenic determinants of a protein.

Synthetic peptides have several advantages as regards the production of specific antibodies and reactivity. The exact sequence of the synthetized peptide can be selected from the amino acid sequence of the protein as determined by the protein amino acid sequence or the predicted amino acid sequence determined by the DNA sequence codified by the protein.

The use of specific synthetic peptides eliminates the need of the protein of complete length in vaccination and production of an assay for antibodies. Also, the synthetic techniques of solid phase peptides of Marrield and co-adjuvants enable to chemically produce them for essentially unlimited amounts of the synthetic peptide of interest. An advance has been produced in said techniques due to the capacity of automatized peptide synthesizers.

In a particular embodiment of the invention, the peptide consisting of SEQ ID NO: 1 is selected for its use as medicine.

In another aspect of the invention, a peptide, essentially consisting of the amino acid sequence of SEQ ID NO: 2 is provided.

In another aspect of the invention, a peptide, essentially consisting of the amino acid sequence of SEQ ID NO: 3 is provided.

In another aspect of the invention, a peptide, essentially consisting of the amino acid sequence of SEQ ID NO: 4 is provided.

In another aspect of the invention, a peptide, essentially consisting of the amino acid sequence of SEQ ID NO: 5 is provided.

In another aspect of the invention, a peptide, consisting of any of the amino acid sequences of SEQ ID NO: 2, SEQ ID NO: 3, SEQ ID NO: 4 or SEQ ID NO: 5 or any of their combinations is provided.

In a preferred embodiment of this aspect of the invention, a peptide consisting of the amino acid sequence of SEQ ID NO: 2 is provided.

In another aspect of the invention, a peptide is provided with an amino acid sequence presenting an identity with any of the peptides essentially consisting of the amino acid sequences of SEQ ID NO: 2, SEQ ID NO: 3, SEQ ID NO: 4 or SEQ ID NO: 5 of, at least, 80%. More preferably, it has an identity of at least 95%, and even more preferably, it has an identity of at least 98%, with said amino acid sequences.

Peptides are useful as vaccines to protect against future infections by nematodes or to promote the immune response against the nematode infection in subjects or animals already infected by nematodes. Although any human subject can be vaccinated with peptides, the most appropriate subjects are people or animals with risk of suffering from nematode infection.

Synthetic polypeptides can also be prepared by expression of one host cell containing a recombinant DNA molecule comprising a sequence of nucleotides which is transcribed to the peptides, operatively joined to a control sequence of the expression, or a vehicle or cloning vector of recombinant DNA containing such recombinant DNA molecule. Alternatively, the peptides can be expressed by direct injection of a simple DNA molecule in a host cell. Generally, the synthetic peptides produced according to the invention represent protective antigenic sequences. The expression "protective antigen", as used in the present invention, defines those antigens capable of generating a protective immune response (immunogenic) of the host, that is, a host answer, which leads to the generation of immune effector molecules, antibodies or cells which sterilize or reduce the fecundity of the parasite or damage, inhibit or kill it, thus "protecting" the host against a clinical or sub-clinical illness and against a loss of productivity. Such protective immune response can be normally manifested by the generation of antibodies which can inhibit the parasite metabolic function, leading to a prevention of its normal growth, lack of egg production and/or death.

The synthetic polypeptide thus expressed can be a fusion polypeptide comprising a part which spreads the immunogenicity of all or a part of the catalytic subunit of the phosphatase Serine/threonine protein of *Angiostrongylus costarricensis*, and an additional peptide codified by the DNA of the recombinant molecules fused to it.

According to another aspect of the present invention, there are provided molecules of nucleic acid comprising one or more sequences of nucleotides, which codify all or part of the peptide codified by the amino acid sequence of SEQ ID NO: 2, SEQ ID NO: 3, SEQ ID NO: 4 or SEQ ID NO: 5, or any of their combinations.

According to another aspect of the present invention, there are provided molecules of nucleic acid comprising one or more sequences of nucleotides, which codify all or part of the peptide codified by the amino acid sequence of SEQ ID NO: 1 or fragments thereof, SEQ ID NO: 2, SEQ ID NO: 3, SEQ ID NO: 4 or SEQ ID NO: 5, or any of their combinations to be used as medicine.

The provision of a nucleic acid molecule according to the invention makes it possible to obtain the peptide of the catalytic subunit of the phosphatase Serine/threonine protein of *Angiostrongylus costarricensis*, or its immunogenic fragments, in amounts not available to date, thus allowing the development of compositions and preferably pharmaceutical compositions.

In this aspect of the invention, it is provided a method to prepare a recombinant protein or peptide codified by a molecule of nucleic acid of the invention, comprising the culture of a eukaryotic or prokaryotic cell comprising a molecule of nucleic acid of the invention, in conditions in which said protein or peptide is expressed, and the recovery of said thus produced peptide.

This method includes the cloning and expression vectors comprising the molecules of nucleic acid of the invention. Such expression vectors include appropriate control sequences, such as, for example, control elements of the translation (as initiation and stop codes) and of the transcription (for example, promoter-operator regions, union sites). The vectors according to the invention can include plasmids and virus (comprising bacteriophages and eukaryotic virus), according to well-known procedures and documented in the art, and can be expressed in a variety of different expression systems, also well-known documented in the art. The appropriate viral vectors include baculovirus and adenovirus and vaccinia virus. Many other viral and non-viral vectors are described and well-known in the art.

It is also known a variety of techniques which can be used to introduce such vectors in prokaryotic or eukaryotic cells for the expression, or in a germinal line or in somatic cells, to form transgenic animals. Appropriate transformation or transfection techniques are described in the bibliography.

Transformed or transfected prokaryotic or eukaryotic host cells, containing a nucleic acid molecule according to the invention, as it was defined above, also form part of this aspect of the invention.

The sequence expression (identical or homologous) codifiers of the catalytic subunit of the phosphatase Serine/threonine protein of *Angiostrongylus costarricensis*, or its immunogenic fragments, according to the invention, using a series of techniques and known expression systems, including the expression of prokaryotic cells such as *E. coli* and in eukaryotic cells such as yeasts or the system of baculovirus-insect cell or transformed mammal cells and in transgenic animals and plants. In a particularly advantageous way, the nucleotide sequences can be expressed using the transgenic nematode system, such as the system corresponding to the *Caenorhabditis* nematode.

In a particular embodiment of this aspect of the invention, the vector used to clone the gen of the recombinant protein was pGex2TK, and the host where it was expressed was the bacteria *Escherichia coli* strain BL21.

The peptides are formulated in compositions to be used as immunogen. These immunogens can also be used as vaccines in animals, and more particularly in mammals, including humans, or produce a response in the production of antibodies in animals. For the formulation of such compositions, an immunologically effective amount of at least one of the peptides is mixed with an appropriate physiologically acceptable transporter for the administration to mammals including humans. Peptides can be covalently bonded with one another, to other peptides to a transport protein or with other transporters, incorporated in liposomes or other similar vesicles, and/or mixed with a coadjuvant or absorbent as it is known in the field of vaccines. For example, the peptide(s) can be mixed with immunostimulating complexes. Alternatively, the peptides are not coupled and merely mixed with a physiologically acceptable transporter such as a normal buffer or saline compound appropriate for its administration to mammals including humans.

Therefore, and as it was described above, synthetic peptides produced according to the invention have protective antigenic sequences. These protective antigens can generate an immune response (immunogenic) which protects the host, that is, a host response leading to the generation of immune effector molecules, antibodies or cells which sterilize or reduce the fecundity of the parasite or damage, inhibit or kill it, thus "protecting" the host from a clinical or sub-clinical illness and against a loss of productivity. Such protective immune response can be normally manifested by the generation of antibodies which can inhibit the parasite metabolic function, leading to a prevention of its normal growth, lack of egg production and/or death.

As with all immunogenic compositions to produce a response in antibodies, the immunogenically effective amounts of the peptides of the invention must be empirically determined. The factors considered include the immunogenicity of the natural peptide, whether the peptide is made into a complex with a covalent bond to an adjuvant or transport protein or another transporter and through the administration path for the composition, for example, and without limiting to, intravenous, intramuscular, subcutaneous, and as in a particular embodiment of the invention, intranasal, as well as the number of the immunization dose that would be administered. Such factors are known in the field of vaccines and in conformance with the ability of the immunologist who has made such determinations without inappropriate experimentation.

In another aspect of the invention, there are provided antibodies produced after the immunization of an animal, with the peptides essentially consisting of the amino acid sequences SEQ ID NO: 2, SEQ ID NO: 3, SEQ ID NO: 4 or SEQ ID NO: 5, or any of their combinations.

The antibodies of the present invention include mixtures of antibodies generated by immunization of one or several animals with one or several peptides of the present invention. Said antibodies can be purified, or not. The generation and purification of antibodies can be made in the laboratory according to general procedures known in the state of the art.

In a particular embodiment of this aspect of the invention, the animal used for the immunization is a mammal, including humans.

In a preferred embodiment, the animal used for the immunization is a mammal, not including humans.

In another particular embodiment of this aspect of the invention, the antibodies produced after the immunization of the animal are used as medicine.

The antibodies of the present invention can be formulated for their administration to an animal, and more preferably a mammal, including humans, in a variety of forms. Thus, the antibodies can be in sterile aqueous solution or in biological fluids, such as serum. Aqueous solutions can be buffered or non-buffered and have additional active or inactive components. Additional components include salts to modulate the ionic force, preservatives including, but not limiting to, antimicrobial agents, antioxidants, chelating agents, and the like, and nutrients including glucose, dextrose, vitamins and minerals. Alternatively, the antibodies can be prepared for their administration in solid form. Antibodies can be combined with several vehicles or inert excipients, including but without limiting to, agglutinants such as microcrystalline cellulose, tragacanth gum, or gelatin; excipients such as starch or lactose; dispersing agents such as alginic acid or corn starch; lubricants such as magnesium stearate; sliding agents such as coloidal silicon dioxide, sweetening agents such as sucrose and saccharin; or aromatic agents such as mint or methyl salicylate.

Antibodies or their formulations can be administered to an animal, including a mammal and, therefore, humans, in a variety of forms. Such ways of administrations include, but are not limited to, intraperitoneal, intravenous, intramuscular, subcutaneous, intrathecal, intraventricular, oral, enteral, parenteral, intranasal or dermal.

The dosage of antibodies to obtain a pharmaceutically effective amount depends on a variety of factors, such as for example, the age, weight, gender, tolerance, . . . of the animal.

In another aspect of the invention, it is provided a composition comprising a peptide of the invention, or an antibody of the invention.

In a preferred embodiment of this aspect of the invention, the composition also comprises pharmacologically acceptable excipients.

In a preferred embodiment of this aspect of the invention, the composition is used as medicine.

In another aspect of the invention, the composition is used in the production of a vaccine.

In the context of the present invention, the term "vaccine" refers to an antigenic preparation used to establish the response of the immune system to an illness. They are preparations of antigens which, once inside the organism, produce the response of the immune system through the production of antibodies, and generate immunologic memory producing permanent or transitory immunity.

In another aspect of the invention, it is provided a vaccine comprising a peptide essentially consisting of the amino acid sequence of SEQ ID NO: 1 or fragments thereof, SEQ ID NO: 2, SEQ ID NO: 3, SEQ ID NO: 4 or SEQ ID NO: 5, or any of their combinations or a nucleic acid molecule which can be transcribed to any of them.

In a preferred embodiment of this aspect of the invention, the vaccine also comprises an adjuvant.

In this memory, the term "adjuvant" refers to an agent which, while not having an antigenic effect by itself, can stimulate the immune system increasing its response to the vaccine. Although not being limited to them, aluminum salts "aluminum phosphate" and "aluminum hydroxide" are the two most commonly used adjuvant in vaccines. Other substances, such as for example, squalane, can also be used as adjuvants.

In another preferred embodiment of this aspect of the invention, the vaccine also comprises the subunit b of the choleric toxin.

The subunit b of the cholera toxin has been shown to induce an immune response against the antigen of interest.

In another preferred embodiment of this aspect of the invention, any of the peptides with the amino acid sequence SEQ ID NO: 2, SEQ ID NO: 3, SEQ ID NO: 4 or SEQ ID NO: 5 it is polymerized with the subunit b of the cholera toxin.

In a more preferred embodiment of this aspect of the invention, the peptide which is polymerized with the subunit b of the cholera toxin contains the amino acid sequence of SEQ ID NO: 2.

In an even more preferred embodiment of this aspect of the invention, the vaccine also comprises the ISCOM matrix.

ISCOM type matrixes are known in the technical field of vaccines, and they are, for example, but without limiting to, those described in patents ES2029758, ES2195169, ES2214608, ES2210495, ES2199346, ES2284265 and their embodiments.

In another embodiment of the invention, the vaccine or the composition is used to prevent parasitization by nematodes of an animal, including a mammal, and therefore humans.

Another aspect of the invention provides a composition comprising one or more peptides according to the invention, a molecule of nucleic acids according to the invention, an antibody according to the invention, or any of their combinations, for use in the preparation of a medicament for the prevention or treatment of the infection by nematode parasites of an animal.

An alternative method of the production of vaccines is the use of molecular biology techniques to produce a fusion protein containing one or more of the peptides of the present invention and a highly immunological protein. For example, fusion proteins containing the antigen of interest and subunit b of the cholera toxin have been shown to induce an immune response against the antigen of interest.

Another aspect of the invention is constituted by a composition comprising a DNA genetic construction, which would direct the in vitro or intracellular transcription of the nucleic acid molecules of the invention, and which comprises, at least, one of the following types of sequences:

a) DNA nucleotide sequence, preferably double chain, comprising, at least, the codifying sequence of any of the amino acid sequences of SEQ ID NO: 1, SEQ ID NO: 2, SEQ ID NO: 3, SEQ ID NO: 4 or SEQ ID NO: 5, for their in vitro or intracellular transcription, or, b) DNA nucleotide sequence, preferably double chain, corresponding to a system or vector of genetic expression comprising the codifying sequence of the sequences according to a) operatively bonded to, at least, a promoter which directs the transcription of said sequence of nucleotides of interest, and with other necessary or appropriate sequences for the transcription and its appropriate regulation in time and place, for example, start and finish signals, cutting places, polyadenylation signal, origin of replication, transcriptional enhancers, transcriptional silencers, etc. Many of these expression systems or vectors can be obtained by conventional methods known by experts in the subject and form part of the present invention.

In a preferred embodiment of this aspect of the invention, the composition containing the genetic construction which allows the transcription and translation of in vitro or intracellular peptides can generate antibodies and can be used in the production of therapeutic vaccines to generate a humoral immune response.

DEFINITIONS

The term "medicine", as used in this memory, refers to any substance used for the prevention, diagnosis, relief, treatment or healing of human and animal illnesses. In the context of the present invention it also refers to a composition capable of generating an immune response against a given parasite which is causing said illness in humans or animals. Therefore, it includes what is known as a vaccine, as it was defined above in this memory.

The term "peptide", as used in the present invention, includes both the full-length protein and the shorter peptide sequences.

The term "antigen", as used in this memory, refers to a molecule (generally a protein or polysaccharide) of cellular surface, which can induce the formation of antibodies. There are many different types of molecules which can act as antigens, such as proteins or peptides, polysaccharides and, more rarely, other molecules such as nucleic acids. Specifically, in this memory, the term antigen would make reference to the catalytic subunit of the phosphatase Serine/threonine protein of *Angiostrongylus costarricensis*, or antigenic fragments thereof, such as, but without limiting to, amino acid sequences of SEQ ID NO: 2, SEQ ID NO: 3, SEQ ID NO: 4 or SEQ ID NO: 5.

The phosphatase Serine/threonine family belongs to the group of phosphatases, which dephosphorylate different proteic residues. Many cellular functions in eukaryotes, including signal transduction, cellular adhesion, transcription, RNA splicing, apoptosis and cellular proliferation are controlled by protein dephosphorylation. Reversible phosphorylation is regulated by the dynamic relation between kinase and phosphatases. There exist three types of eukaryotes:

Serine/threonine Phosphatases (PSTPs)
Protein Tyrosine Phosphatases (PTPs) and
Dual Specificity Phosphatases (DSPs)

PSTPs are phosphatases with a majority of eukaryotes and they have been isolated and characterized by a great number of tissues. They are classified in subfamilies according to the specificity of the substrate, dependence to metallic ions and sensibility to inhibitors.

Most PSTPs are multimeric proteins formed by a catalytic subunit and one or more accessory proteins. Accessory proteins confer specificity to the substrate, regulate the enzymatic activity and control the subcellular localization of holoenzyme (Faux, M. C. & Scott, J. D. 1996. More on target with protein phosphorylation: conferring specificity by location. *Trends Biochem. Sci.* 21, 312-315).

Proteins of the subfamily PP2A can be dimeric or trimeric, generally comprise a catalytic subunit (C), a structural subunit (A) and a regulatory subunit (B). Subunit A or structural subunit is the union between the subunit C and B, where the subunit B is the one which gives the holoenzyme substrate specificity.

Serine/threonine phosphatase PP2A is the most prevalent in eukaryotes and is mainly cytosolic although it can be found in the nucleus, it intervenes in numerous vital processes such as: mitosis, apoptosis, replication and DNA damage repair, signal transduction, response to stress caused by heat.

In species such as Drosophila melanogaster, the catalytic subunit of PP2A protein intervenes in the regulation of the cellular cycle and intracellular signalization, being expressed in all phases although it is notably greater in early embryos. It has been possible to confirm the role of PP2A in the morphogenesis and mitosis.

Members of the family of serine/threonine phosphatase have been identified in nematodes so far in Trichinella spiralis, Caenorhabditis elegans, Oesophagostomum dentatum, Trichostrongylus vitrinus. In Trichostrongylus vitrinus and Oesophagostomum dentatum serine/threonine phosphatases have been related to reproductive processes and there exist records relating them to spermatogenesis and/or sperm mobility.

Both isoforms are highly expressed in the brain and heart, although PP2Acα is ten times more abundant than PP2ACβ. There have also been isolated several species in different types of tissues, in mammals there have been isolated from the liver, lung and brain, among others.

The identification of PP2AC in organisms such as: Xenopus, Drosophila, plants Brassica napus and Arabidopsis thaliana, and yeasts Schizosaccharomyces pombe and Saccharomyces cerevisiae have revealed that PP2Acs can be the most conserved of all known enzymes.

The "structural subunit" A is a protein of 65 kD, which is associated to PP2Ac forming a dimer to which subunit B is joined. As PP2Ac, the structural subunit in mammals is codified in two genes alpha and beta, which have 87% of identity. In general, PR65 alphaβ is more abundant than PR65 beta, except in Xenopus oocytes, being PR65 betaβ highly expressed in the ovary during oogenesis, meiosis, maturation and fertilization. PR65β has been identified as a tumor inhibitor in humans. This enzyme shows a 15% of somatic alterations in the gen codifying PR65 beta in carcinogenic cell lines of lung and colon. These alterations include gene deletions, internal deletions and in C-terminal of the protein. Recently, there have been detected mutations in which the isoform PR65 alpha is codified in human breast and lung melanomas and carcinomas, although said mutations occur in a low proportion when compared to studies performed with PR65 beta.

The PR65 structure comprises 15 repetitions by tandem of 39 amino acids, called HEAT, this tandem repetition is found in several proteins including elongation factors and TOR kinases. The crystallization of PR 65 revealed that the architecture of each repetition is virtually the same, two alpha helixes.

The third subunit associated to this holoenzyme is the subunit B. there exist three types of subunit B described: PR55, PR61 and PR93/PR110. The "regulating subunit" PR55 is a protein of 55 kDa which is codified in four genes (PR55 alpha, PR55 beta, PR55 Gamma and PR55 delta) in mammals, which are expressed in specific tissues. PR55 alpha and PR55 delta have a wide distribution in tissues, while PR55beta and PR55 gamma are highly concentrated in the brain.

The uniform presence of subunits A and C indicate that subunits B confer a subcellular localization, providing regulation and specificity to the holoenzyme PP2A. The specific union of each subunit B gives the substrate specificity and location.

In spite of the fact that there only exist two isoforms of the subunit C of holoenzyme PP2A, the potential number of associations of the two subunits A and of the four subunits B is very high, this makes an approximate total of 75 different trimeric holoenzyme PP2A. This specific composition provides many possibilities for the regulation and is tissue specific.

Additionally, in the identification of an amino acid sequence belonging to the catalytic subunit of serine/threonine kinase the following parameters are applicable, either individually or in combination. As DNA sequences are similar regarding their evolution, it can be expected that the global identity of the genomes at the amino acid level, and more specifically at the level of amino acid sequence which is found in the SEQ ID NO: 1, be 80%, or higher, and more preferably 90% or higher, and even more preferably 95% or higher.

In the sense used in this description, the expression "therapeutically effective amount" refers to the amount of peptides, antibodies or antibody fragments, or genetic constructions which enable their expression calculated to produce the desired effect and, generally, it will be determined, among other causes, by the characteristics of said peptides, antibodies, sequences and constructions and the therapeutic effect to be attained. The adjuvants and pharmaceutically acceptable vehicles can be used in said compositions in the vehicles known by experts in this matter. The compositions provided by the present invention can be administered by any means; therefore, said composition will be formulated in the form that is pharmaceutically appropriate for the chosen administration path.

Along the description and the claims the word "comprises" and its variants do not intend to exclude other technical characteristics, additives, components or steps. For experts in the subject matter, other objects, advantages and characteristics of the invention will be derived partly from the description and partly from the practice of the invention. The following examples and drawings will be provided as illustration and they are not intended to be limiting for the present invention.

BRIEF DESCRIPTION OF THE DRAWINGS

FIG. 1 shows the homology of the sequence with the catalytic domain of the serine/threonine phosphatase family 2A. Therefore, we will determine that the sequence identified would correspond to the catalytic subunit of the serine/threonine phosphatase family 2A.

FIG. 2 shows the consent between the catalytic domain of cd00144, PP2Ac, homologous to phosphatase 2A protein, catalytic domain and amino acid sequence of the protein "serine/threonine phosphatase pph-1", Expect 3e-15.

DETAILED EXPOSITION OF EMBODIMENTS

Next, the invention will be illustrated through assays performed by the inventors, which show the specificity and effectiveness of synthetic peptides and the recombinant protein for the generation of an immune response against nematodes.

Example

In order to identify target proteins with antigenic characteristics a cDNA library was made from the adult nematode Angiostrongylus costarricensis, which was traced with a pool of serum from patients with the illness which produces abdominal angiostrongyliasis. From these traces it was possible to identify a clone with a 345pb sequence corresponding to a 76 amino acid sequence, which was deposited in EMBL as "serine/threonine phosphatase pph-1" (AM041130) and in this memory it corresponds to the SEQ ID NO: 1.

FIG. 2 shows the homology of the sequence with the catalytic domain of the serine/threonine phosphatase 2A family. Therefore, it is determined that the sequence identified corresponds to the catalytic subunit of the serine/threonine phosphatase 2A family.

Production of the Synthetic Peptide

In order to verify the antigenic characteristics of the protein, the amino acid sequence was analyzed with the antigenic program of the EMBOSS package (Kolaskar, A S & Tongaonkar, P C. 1990. A semi-empirical method for prediction of antigenic determinants on protein antigens. FEBS Letters 276: 172-174), and as a result of said analysis 4 peptides were obtained. The peptide selected for the example was ANFIIFRPVV.

Production of Antigens

For the immunoprotection assays the polymerized synthetic peptide and the recombinant protein (serine/threonine phosphatase pph-1) were used as antigen.

Recombinant Protein

The gene corresponding to said recombinant protein was subcloned in the pGex2TK vector and obtained from the culture of the *Escherichia coli* bacteria strain BL 21.

Production of Subunit B of the Cholera Toxin

The subunit b of the cholera toxin is obtained from the commercial cholera toxin.

Polymerization of the Synthetic Peptide

For the polymerization of the synthetic peptide, Endoh et al. 1981 (Antibody coating of liposomes with 1-ethyl-3-(3-dimethyl-aminopropyl)carbodiimide and the effect on target specificity. *J Immunol Methods.;* 44(1):79-85) technique was used. 2 mg of synthetic peptide were used and mixed with 3 mg of subunit b of the cholera toxin, and dissolved with 20 ml PBS. Once dissolved 40 µl glutaraldehyde was added and incubated at room temperature for 6 hours. The relation was stopped with the addition of 1 ml glycine 1 M, and incubated again at room temperature for 30 minutes and finally dialyzed for 12 hours at 4° C. This procedure was performed with the synthetic peptide with the subunit b of the cholera toxin.

Preparation of ISCOM

Nano capsules were prepared using the technique described by losef C et al., 2002 (Systemic and intestinal antibody secreting cell responses and protection in gnotobiotic pigs immunized orally with attenuated Wa human rotavirus and Wa 2/6-rotavirus-like-particles associated with immunostimulating complexes. *Vaccine;* 15; 20(13-14): 1741-1753) later modified by P H.-Demana et al., 2004 (Pseudo-ternary phase diagrams of aqueous mixtures of Quil A, cholesterol and phospholipid prepared by the lipid-film hydration method. Int J. Pharm. 2004 Feb. 11; 270(1-2):229-39). Once prepared, they were mixed in a 1:1 ratio with the synthetic peptide polymerized with and without subunit b of the cholera toxin. Later, it was dialyzed making 4 changes of 12 hours, the samples were lyophilized and their correct formation was verified by electronic microscopy.

Immunoprotection Assay

Six groups of 5 mice C57Bl/6 were used, which were immunized intranasally with 5 µg of encapsulated antigens in ISCOM (polymerized peptide and polymerized peptide with subunit b of cholera toxin) and 50 µg total proteins (bacterial proteins and recombinant protein). Two intranasal inoculations were made, with an intermediate period of 15 days. One month after the second inoculation the oral infection with 3 third stage larvae of the nematode and the slaughtering were performed and the results were verified one month after the infection.

Each one of the slaughtered mice was examined in search of alterations and presence of adult nematodes, finding an 80% reduction of the parasite load in the group inoculated with the synthetic peptides in combination with the cholera toxin and a 100% reduction in the group inoculated with the recombinant protein.

The invention claimed is:

1. A method for prevention or treatment of parasitization by nematodes of an animal, comprising administering to the animal a therapeutically effective amount of a composition comprising a peptide having the amino acid sequence of SEQ ID NO:1.

2. A method for prevention or treatment of parasitazion by nematodes of an animal, comprising administering to the animal a therapeutically effective amount of:
   a peptide whose amino acid sequence has at least 80% homology with SEQ ID NO: 1.

3. A method for prevention or treatment of parasitazion by nematodes of an animal, comprising administering to the animal a therapeutically effective amount of a vaccine comprising a peptide having the amino acid sequence of SEQ ID NO:1.

4. The method for prevention or treatment according to claim 2, wherein the peptide is found or transduced in a therapeutically effective amount capable of generating antibodies for use in production of vaccines.

* * * * *

SEQUENCE LISTING

```
<160> NUMBER OF SEQ ID NOS: 5

<210> SEQ ID NO 1
<211> LENGTH: 76
<212> TYPE: PRT
<213> ORGANISM: Angiostrongylus costaricensis

<400> SEQUENCE: 1

Val Val Asp Glu Phe Cys Thr Asn His Asn Ile Asp Leu Ile Leu Arg
1               5                   10                  15

Ala His Gln Ile Thr Ala Glu Met Val Tyr Gly Gly Tyr Arg Ile Phe
            20                  25                  30

Ala Gly Gly Arg Leu Val Thr Ile Phe Ser Ala Pro Asn Tyr Gln Asn
        35                  40                  45

Met Met Asn Asp Gly Cys Val Met Arg Ile Lys Arg Asp Leu Thr Ala
    50                  55                  60

Asn Phe Ile Ile Phe Arg Pro Val Val Arg Arg His
65                  70                  75

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 2
```

```
Ala Asn Phe Ile Ile Phe Arg Pro Val Val
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Gly Gly Arg Leu Val Thr Ile Phe Ser Ala Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Ile Asp Leu Ile Leu Arg Ala His Gln Ile
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 5

Ala Glu Met Val Tyr Gly Gly Tyr Arg Ile Phe
1               5                   10
```